US006187341B1

(12) United States Patent
Johnson et al.

(10) Patent No.: US 6,187,341 B1
(45) Date of Patent: Feb. 13, 2001

(54) TROVAFLOXACIN MESYLATE TABLET

(75) Inventors: Alton D. Johnson, New York, NY (US); Christopher M. Sinko, Niantic, CT (US)

(73) Assignee: Pfizer Inc., New York, NY (US)

(*) Notice: Under 35 U.S.C. 154(b), the term of this patent shall be extended for 0 days.

(21) Appl. No.: 09/233,823

(22) Filed: Jan. 20, 1999

Related U.S. Application Data

(60) Provisional application No. 60/072,013, filed on Jan. 21, 1998.

(51) Int. Cl.[7] .................................. A61K 9/32; A61K 9/36
(52) U.S. Cl. .......................... 424/480; 424/464; 424/465; 424/489; 424/474; 514/781
(58) Field of Search ................................ 424/464, 465, 424/489, 480, 474, 482

(56) References Cited

U.S. PATENT DOCUMENTS

| 5,286,754 | 2/1994 | Streuff et al. .................... 514/772.3 |
| 5,464,796 | 11/1995 | Petersen et al. ................... 514/312 |

FOREIGN PATENT DOCUMENTS

| 0230881 | 8/1987 | (EP) | ............................. A61K/31/495 |
| 0413456 | 2/1991 | (EP) | ............................. C07D/401/04 |
| 2056411 | 6/1992 | (RU) | ............................. C07D/215/56 |
| WO9707800 | 3/1997 | (WO) | ............................. A61K/31/435 |

OTHER PUBLICATIONS

Voigt, R., Pharmazeutische Technologie Für Studium Und Beruf, 1993, pp. 208–213 (English Translation).

*Primary Examiner*—James M. Spear
(74) *Attorney, Agent, or Firm*—Peter C. Richardson; Gregg C. Benson; Michelle A. Sherwood

(57) ABSTRACT

Compositions, especially in the form of tablets containing the polymorph II form of trovafloxacin mesylate, a lubricant, and microcrystalline cellulose (MC) as the diluent. Such compositions employing MC as a diluent exhibit good storage stability properties and dissolution.

16 Claims, No Drawings

TROVAFLOXACIN MESYLATE TABLET

This application is filed claiming priority from co-pending Provisional Application Ser. No. 60/072,013, filed Jan. 21, 1998.

FIELD OF THE INVENTION

This invention relates to a tablet dosage form of trovafloxacin mesylate.

BACKGROUND OF THE INVENTION

Trovafloxacin is a quinolone antibiotic having the structure:

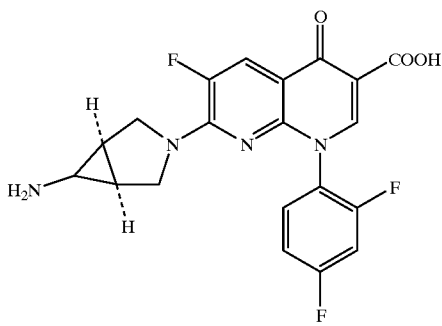

It is currently administered in the form of the mesylate salt. Trovafloxacin and its mesylate salt are disclosed and claimed in U.S. Pat. No. 5,164,402, incorporated herein by reference.

Trovafloxacin mesylate can exist in a number of polymorphic forms as disclosed in PCT/US95/07211 (which designates, inter alia, the United States), which has been published as WO 96/39406, and which is herein incorporated by reference. The polymorphs are also disclosed in the Analyst, June 1997, V. 122, pp. 549–552 as Polymorph I, Polymorph II, and the mesylate monohydrate. Polymorph II, in particular, is an anhydrate which is stated to be hydrophobically stable such that formulation problems of the active ingredient during tabletting or encapsulation operations are alleviated. Polymorph I, also an anhydrate, is disadvantageous in that it is reported to be substantially hygroscopic such that it picks up water from the atmosphere to form a monohydrate, a third form of trovafloxacin. Reference to polymorphs in this application utilizes the same nomenclature designations as in the Analyst article for the sake of continuity.

When formulating a compound into a tablet (or other) dosage form, one typically seeks, inter alia, a formulation which is storage stable at temperatures and relative humidity levels above those typically encountered. One may additionally seek other desirable properties in a formulation such as fast dissolution so that the tablet quickly dissolves and the medicine is available for absorption, and also properties such as good compressibility and high ductility, and ease of formulatability in general. Accordingly, good storage stability and fast dissolution were, inter alia, features that were sought as desirable characteristics for the instant invention.

Surprisingly, only a single diluent or filler among many tested provided good storage stability and dissolution in conjunction with good manufacturability.

SUMMARY OF THE INVENTION

This invention relates to a tablet having good storage stability and exhibiting many formulation advantages. In the discussion which follows and elsewhere herein, designation of amounts in "%" means % by weight based on the weight of an uncoated tablet.

This invention provides a tablet comprising the Polymorph II form of trovafloxacin mesylate, a lubricant, and at least 5% of microcrystalline cellulose (MC). The uncoated tablet preferably comprises at least 20% of microcrystalline cellulose, more preferably at least 30%. "Microcrystalline cellulose" is used for its conventional, art-recognized meaning, i.e., partially depolymerized cellulose obtained from α-cellulose. It is noted that Polymorph II is characterized by the following X-ray powder diffraction pattern (reproduced from WO 96/39406):

Polymorph II (B 2) Anhydrous

| Peak no. | 1 | 2 | 3 | 4 | 5 | 6 | 7 | 8 |
|---|---|---|---|---|---|---|---|---|
| 2θ (°) Cu | 4.5 | 7.7 | 9.1 | 13.6 | 15.0 | 18.2 | 18.6 | 22.8 |
| d space | 19.5 | 11.5 | 9.7 | 6.5 | 5.9 | 4.9 | 4.8 | 3.9 |

Necessary ingredients in the tablet core thus include lubricant, trovafloxacin mesylate, and MC. If the MC is present in an amount below about 10%, then it is preferred that a disintegrant also be present in an amount at least equal to the weight % amount of MC that would be needed to bring the actual amount of MC up to 10%. For example, if the tablet contains 8% MC, it is preferred that the tablet additionally contain at least 2% of a disintegrant. If the MC is present in an amount of at least 10%, then no other excipients in addition to the lubricant, such as the disintegrating agent, are needed, although the addition of such may improve dissolution specifications.

In addition to trovafloxacin mesylate, lubricant, and MC, other common excipients can also be employed in the compositions of this invention. As mentioned above, a disintegrant is desirable when the amount of MC is less than 10%, but can also be useful when the amount of MC exceeds 10%. Other excipients in addition to disintegrants, including binders, lubricants, flavorings, colors, and glidants may also be useful. Some excipients can serve multiple functions, for example as both binder and disintegrant.

The tablet is desirably coated with a conventional film coating which imparts toughness, ease of swallowing, and an elegant appearance to the final product. Film coatings made entirely or partially from hydroxypropylcellulose (HPC) are preferred, although film coating polymers having equivalent toughness can be used as well. The film former used to form the film coat can also contain hydroxypropylmethylcellulose (HPMC). Use of a film coating is preferred because it improves light stability of the dosage form.

The invention is surprising because microcrystalline cellulose is one among many conventional diluents employed in the pharmaceutical arts, a diluent being an inert excipient which has no function other than to add mass to a solid dosage form. Other common diluents include, for example, calcium salts such as calcium phosphate dibasic, calcium sulfate, and calcium carbonate and sugars such as lactose, sucrose, dextrose, maltodextrin, and mannitol. Yet it has been determined that the combination of microcrystalline cellulose with Polymorph II of trovafloxacin mesylate produces a tablet which is highly storage stable in the sense that the uncoated tablet retains its chemical stability such that there is little if any degradation of trovafloxacin mesylate or excipients upon extended storage. Other diluents such as calcium phosphate were found to suppress the dissolution profile after storage, and diluents such as sugars were found to result in degradation of the trovafioxacin mesylate after storage. Polymorph I was found to convert to the mesylate monohydrate form during storage.

Compositions (i.e., uncoated tablets) according to the invention can be dissolution tested in a USP-2 apparatus in 900 mL of aqueous $KH_2PO_4$ at pH 2, concentration 50 mM, with paddles rotating at 50–100 RPM. Compositions according to the invention exhibit at least the acceptance criteria cited for Stage 1 ($S_1$) testing in the USP 23 (*The United States Pharmacopeia*, edited by the United States Pharmacopeial Convention, Inc., 12601 Twinbrook Parkway, Rockville, Md. 20852; Published by Rand McNally, Inc., 23rd Edition, Copyright 1994):

| Stage | Number Tested | Acceptance Criteria |
|---|---|---|
| $S_1$ | 6 | Each unit not less than Q + 5% | where Q in this case is 80% dissolution of trovafloxacin within 30 minutes after insertion of the uncoated tablet into the phosphate buffer.

Compositions according to the invention made using magnesium stearate as a lubricant can be stability tested in vitro by storing the tablets for 12 weeks in an open container at constant conditions of 40° C and 75% relative humidity. After the 12 week period has elapsed, each composition is tested for degradants by high performance liquid chromatography (HPLC) and/or thin layer chromatography (TLC). Compositions within the scope of the invention exhibit a degradant level less than the following A. less than 0.5% by weight of each of the following two specific compounds, N-stearoyltrovafloxacin and N-palmitoyltrovafloxacin labeled as formulas (I) and (II):

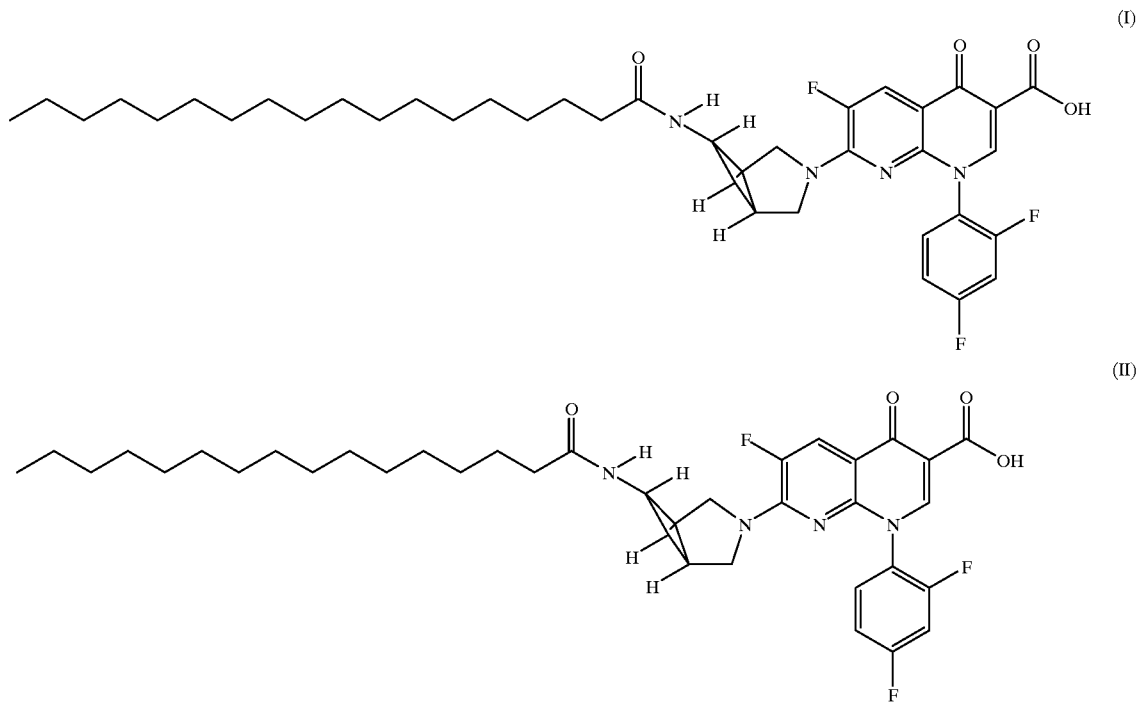

B. less than 0.2% by weight of any other unspecified degradant, regardless of source; and C. the total of all degradants (i.e., (A)+(B)) is less than 1.0% by weight.

When conducting the chemical stability test, sample preparation can be effected using the untabletted tablet blend. Alternatively, sample preparation can be effected using one or more tablets. An amount of blend or tablet sufficient to achieve a final concentration of 50 µg/mL of trovafloxacin is prepared using HPLC mobile phase (see below for examples) as the sample solvent. Serial dilutions with mobile phase may be necessary depending on the amount of sample used. If the tablet blend is employed, sonication is desirable to ensure complete dissolution of the sample. If one or more tablets are employed as the sample, mechanical shaking (e.g., using a mechanical shaker such as a Janke & Kunkel, Model HS500), usually for an hour or more, should be employed to ensure complete disintegration and dissolution in the HPLC mobile phase.

An example of a suitable HPLC assay to detect degradant compounds (I) and (II) is one conducted reverse phase to separate trovafloxacin from dependent compounds (I) and (II). Comparison of the peak area response and retention times for a tablet and working standards provides a quantitative assay and identification test for trovafloxacin and for degradants (I) and (II). The test can be conducted with equipment and methodology well known to the art, such as a Waters Puresilo® $C_{18}$ HPLC column, 15 cm in length×4.6 mm ID, column temperature of 35° C, with an isocratic mobile phase of (degassed) acetonitrile/water/trifluoroacetic acid in a ratio of 900/100/1, v/v/v, and at a flow rate of 1 mL/min. Detection is UV at 270 nm. The analysis (run) time is generally about 20 minutes. The trovafloxacin is essentially unretained and elutes with the solvent front. The retention time for N-stearoyltrovafloxacin (compound (I)) is usually about 16 minutes. The relative retention time for compound (II), measured against N-stearoyltrovafloxacin, is about 0.6. The abundance of these degradants are calculated by determining the area of the peak and then using the following formula:

$$\text{Abundance, \%} = \left[\frac{Ai \times DF \times 100}{R(avg) \times LC}\right]$$

where $A_i$=area of peak in sample
DF=dilution factor=sample dilution:standard dilution
$R_{(avg)}$=average standrad response factor for N-stearoyltrovafloxacin
LC=label claim of tablet, mg The standard response factor for N-stearoyltrovafloxacin is determined by:

$$R = \left[\frac{A}{Ws \times PF}\right]$$

where

A=area of N-stearoyltrovafloxacin peak in standard
$W_s$=weight of the working standard used, mg
PF=purity factor of the working standard Degradants other than compounds (I) and (II) can be quantified using the same HPLC system as described above, except that the isocratic mobile phase is 25% (v/v) acetonitrile and 75% (v/v) 0.05 M $KH_2PO_4$ buffer (made with purified water) having a pH of 2.5. The pH can be adjusted up or down using potassium hydroxide or hydrochloric acid, typically 0.1–0.5 M, as required. This method is useful for observing degradants that are more polar or slightly less polar than trovafloxacin. Using this method, degradants have been observed as peaks on a chromatogram that have distinctly different retention times from the main peak associated with trovafloxacin. Trovafloxacin elutes at approximately 4.5 minutes. Degradants have been observed at the following relative retention times: 0.6, 0.7, 0.9, 1.2, 1.4, 1.6, 1.9, 2.3, 2.8, 4.0. The degradants are quantified by dividing the area of the peak associated with the degradant in a chromatogram by the area of the peak associated with trovafloxacin mesylate.

Thin layer chromatography can also be employed to identify trovafloxacin and methanesulfonic acid against a working standard of trovafloxacin mesylate, using standard silica gel plates with a 250 μm thickness of silica gel (obtainable from E. M. Science) and a methyl isobutyl ketone (MIK) developing solvent. Dosage form excipients do not interfere with the evaluation. The developing solvent can be made by combining MIK, reagent grade glacial acetic acid, and water in a 2:1:1 ratio (v/v).

If desired, diluents that are non-reactive toward trovafloxacin can be employed in addition to MC in the formulations of this invention, so long as the MC itself is present in an amount of at least 5%. Such other diluents include those which adversely affect dissolution so long as the dissolution specifications noted above are met for the resulting tablet. Such other non-reactive diluents are preferably employed in an amount less than 20%, preferably less than 10%, more preferably 0%.

DETAILED DISCUSSION

Binders are excipients which contribute to particle adhesion in a solid formulation. Examples of binders include acacia, cellulose derivatives (carboxymethylcellulose, hydroxypropyl methylcellulose, hydroxypropyl cellulose, hydroxyethylcellulose, ethylcellulose, microcrystalline cellulose) calcium salts such as calcium phosphate dibasic, calcium phosphate tribasic, calcium sulfate and calcium carbonate and sugars such as lactose, sucrose, dextrose, glucose, maltodextrin, and mannitol, gelatin, xylitol, polymethacrylates, polyvinylpyrrolidone, starch paste, sorbitol, pregelatinized starch, gum tragacanth, alginic acids, and salts thereof such as sodium alginate, magnesium aluminum silicate, polyethylene glycol, guar gum, bentonites, and the like. Generally the amount of binder can be from 0% to 50% by weight.

Disintegrants are excipients which oppose the physical forces of particle bonding in a tablet or capsule when the dosage form is placed in an aqueous environment. Examples of disintegrants can include crosslinked polyvinylpyrrolidone, sodium starch glycolate, crosslinked sodium carboxymethyl cellulose (sodium croscarmellose), and pregelatinized starch. Generally the amount of disintegrant can be from 0 to 25% by weight.

Examples of flavors include synthetic flavor oils and flavoring aromatics and/or natural oils, extracts from plant leaves, flowers, fruits, and so forth and combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil. Also useful as flavors are vanilla, citrus oil, including lemon, orange, grape, lime and grapefruit, and fruit essences, including apple, banana, pear, peach, strawberry, raspberry, cherry, plum, pineapple, apricot, and so forth. The amount of flavoring may depend on a number of factors including the organoleptic effect desired. Flavors need not be included at all, but if included typically comprise 0 to about 3% by weight of the tablet.

Examples of lubricants include magnesium stearate, calcium stearate, sodium stearyl fumarate, stearic acid, glycerylbehaptate, polyethylene glycol, ethylene oxide polymers (for example, available under the registered trademark Carbowax from Union Carbide, Inc., Danbury, Conn.), sodium lauryl sulfate, magnesium lauryl stearate, mixtures of magnesium stearate with sodium lauryl sulfate, and hydrogenated vegetable oil. Preferred lubricants include calcium stearate, magnesium stearate and sodium stearyl fumarate. Most preferred as the lubricant is magnesium stearate. Lubricants generally comprise 0.5 to 7.0% of the total (uncoated) tablet weight. The amount employed is generally about 1 to 5.0%, preferably 0.5 to 2.0%.

Examples of glidants include colloidal silicon dioxide and talc, generally employed in an amount of 0 to 5%.

Examples of colors include titanium dioxide and/or dyes suitable for food such as those known as F. D. & C. dyes and natural coloring agents such as grape skin extract, beet red powder, beta carotene, annato, carmine, turmeric, paprika, and so forth. A coloring agent is an optional ingredient in the compositions of this invention, but when used will generally be present in an amount up to about 4.0%.

In a preferred embodiment, tablets of this invention are film-coated to provide toughness, ease of swallowing and an elegant appearance. Many polymeric film-coating materials are known in the art. A preferred film-coating material is hydroxypropylmethylcellulose (HPMC). HPMC may be obtained commercially, for example from Colorcon Corp., in coating formulations containing excipients which serve as coating aids, under the registered trademark Opadry. Opadry formulations may contain lactose, polydextrose, triacetin, polyethyleneglycol, polysorbate 80, titanium dioxide, and one or more dyes or lakes. Other suitable film-forming polymers also may be used herein, including, hydroxypropylcellulose, vinyl copolymers such as polyvinyl pyrollidone and polyvinyl acetate, and acrylate-methacrylate copolymers.

The amount of trovafloxacin mesylate in the uncoated tablet can be from about 10% to about 90%, preferably from 20% to 80%, more preferably 40% to 80%. At least 5% by weight of the uncoated tablet should be MC, preferably at least 10%, more preferably at least 20% by weight. MC can comprise up to 90% by weight of the tablet. An amount of MC from 40 to 80% is most preferred.

Preferred trovafloxacin tablets of this invention are prepared using a granulation step. The formulation can be processed into tablets by conventional dry granulation methods, that is by blending the trovafloxacin mesylate, microcrystalline cellulose, and other excipients in a dry granulation which is then compressed on a conventional tablet press at pressures of typically 5 to 40 KNewtons. Dry granulation, generally understood to mean roller compaction or slugging, is well known to those skilled in the art as disclosed, for example, in *Pharmaceutical Dosage Forms: Tablets*; Edited by Lieberman, Lachman, and Schwartz; Published by Marcel Dekker, Inc., 2d Edition, Copyright 1989, and also *Remington's Pharmaceutical Sciences*, 18th edition, 1990, edited by A. R. Gennaro, Mack Publishing Co., Easton, Pa., the text of both of which are herein incorporated by reference. Wet granulation is not preferred since it can cause the Polymorph II form of trovafloxacin mesylate to form the monohydrate. The tableting process itself is otherwise standard and readily practiced by forming a tablet from a desired blend or mixture of ingredients into the appropriate shape using a conventional tablet press.

Tablets prepared as described above can be conventionally film coated. The coating preferably comprises hydroxypropyl cellulose (HPC) having a viscosity of 75 mPas (milli Pascal-seconds), measured at 5% (w/v) in water by using a Brookfield Model LVT Synchro-Lectric viscometer equipped with a U.L. adaptor. Other conventionally employed film forming polymers, for example hydroxypropyl methylcellulose, can be used in addition to HPC, or instead of HPC so long as the polymer exhibits equivalent toughness to HPC. The film coating can be applied by conventional methodology, for example by using a side vented coating pan.

The invention is further disclosed and described by means of the following examples, which are not to be taken as limiting.

EXAMPLE 1

The following composition of matter is a formulation which was made in accordance with the principles herein.

| Component | %, w:w |
|---|---|
| Trovafloxacin Mesylate* | 52.7 |
| Microcrystalline Cellulose | 36.8 |
| Sodium Croscarmellose | 4.8 |
| Magnesium Stearate | 1.9 |
| Opadry ® Blue (Y-5-10670)[1] | 3.8 |

[1]Contains hydroxypropyl methylcellulose, hydroxypropyl cellulose, titanium dioxide, polyethylene glycol, FD&C Blue #2 lake
*polymorph II The trovafloxacin mesylate, Polymorph II, MC, sodium croscarmellose and one half of the magnesium stearate were blended in a tumbling blender, then dry granulated using a Freund TF Mini roller compactor with a pressure setting of 40 $Kg_f/cm^2$ and then milled with an oscillating granulator using a 20 mesh screen. The remaining magnesium stearate was added to the granulation and blended prior to compression on a conventional tablet press. The tablet cores were then coated with an aqueous suspension of the Opadry® (registered trademark of Colorcon Inc. for a series of film coating systems) Blue.

EXAMPLE 2

Tablets having the composition of matter shown below, in which lactose was employed as a diluent in addition to MC, were made by wet granulating trovafloxacin mesylate, lactose, MC, hydroxypropyl cellulose and half the amount of crosslinked sodium carboxymethylcellulose with water and drying at 50 C. for 18 hours. The granulation was then passed through a 40 mesh stainless steel screen. The remaining amount of crosslinked sodium carboxymethylcellulose was added and blended. Magnesium stearate was then added and blended to form the final blend. The final blend was compressed into tablets using a Manesty "F"-press.

| Component | %, w:w |
|---|---|
| Trovafloxacin Mesylate* | 57.8 |
| Lactose, anhydrous | 15.0 |
| Microcrystalline Cellulose | 19.2 |
| Hydroxypropyl Cellulose | 2.0 |
| Sodium Croscarmellose | 4.5 |
| Magnesium Stearate | 1.5 |

*polymorph I

The tablets, together with comparison tablets made as in Example 1, were stability tested by storing the tablets for 12 weeks in an open container at constant conditions of 40° C. and 75% relative humidity. After the 12 week period had elapsed, each composition was tested for its degradant profile by HPLC assay conducted reverse phase to separate trovafloxacin from any potential degradation products, process-related compounds, and formulation excipients. Peak areas and retention times for tablets were compared with a working standard to identify and quantify trovafloxacin and identify degradants. The test was conducted with a Waters Puresil® $C_{18}$ HPLC column, 15 cm in length×4.6 mm ID, column temperature of 35° C., with an isocratic mobile phase of 25% (v/v) acetonitrile and 75% (v/v) 0.05 M $KH_2PO_4$ buffer (made with purified water) having a pH of 2.5, and at a flow rate of 1 mL/min. Detection was UV at 270 nm. The tablets of Example 1 exhibited a total impurities level of 0.3%, as compared to the tablets of this example which exhibited a degradation of 2.4%.

EXAMPLE 3

This example demonstrates that diluents other than MC can adversely affect the dissolution properties of trovafloxacin mesylate-containing tablets.

Tablets having the following composition were made by blending trovafloxacin mesylate (polymorph II), calcium phosphate dibasic, dihydrate, sodium croscarmellose and half the magnesium stearate. The blend was then dry granulated via a slugging process on a Manesty F-press. The slugs were then broken apart in a mortar and pestle and passed through a 30 mesh screen. The remaining magnesium stearate was added to the granulation and tablets were compressed using a Manesty F-Press.

| Component | %, w:w |
|---|---|
| Trovafloxacin Mesylate | 54.7 |
| Calcium Phosphate, Dibasic, Dihydrate | 38.3 |
| Sodium Croscarmellose | 5.0 |
| Magnesium Stearate | 2.0 |

Tablets having the above composition were dissolution tested in a USP-2 apparatus with paddles rotating at 50 rpm in 900 mL of pH 2.0 phosphate buffer (50mM), and the result compared with the dissolution results for tablets made as in Example 1. The tablets of Example 1 exhibited 96% dissolution of Polymorph II in 30 minutes. The tablets of this example exhibited an average of 84% dissolution of Polymorph II in 30 minutes thus failing the USP stage 1 ($S_1$) criterion:

| Stage | Number Tested | Acceptance Criteria |
|---|---|---|
| $S_1$ | 6 | Each unit not less than Q + 5% | where Q in this case is 80% dissolution of trovafloxacin within 30 minutes after insertion of the tablet into the phosphate buffer.

EXAMPLE 4

Dissolution testing was conducted as described in Example 3 for tablets having the following composition

| Component | %, w:w |
|---|---|
| Trovafloxacin Mesylate, Polymorph I | 87.5 |
| Citric Acid | 6.5 |
| Sodium Starch Glycolate | 5.0 |
| Magnesium Stearate | 1.0 |

Tablets comprising the composition described in the above table were manufactured according to the process described in Example 3 and compared with the following composition (also made according to the process described in Example 4) in which citric acid was replaced by MC.

| Component | %, w:w |
|---|---|
| Trovafloxacin Mesylate | 87.5 |
| Microcrystalline Cellulose | 6.5 |
| Sodium Croscarmellose | 5.0 |
| Magnesium Stearate | 1.0 |

The former formulation containing citric acid exhibited 5% dissolution in 30 minutes. The latter formulation in which MC replaced citric acid exhibited 100% dissolution in 30 minutes.

EXAMPLE 5

Tablets (uncoated) were made from the following composition outside the scope of the invention:

| Component | %, w:w |
|---|---|
| Trovafloxacin Mesylate, Polymorph I | 87.5 |
| Calcium Sulfate | 6.5 |
| Sodium Starch Glycolate | 5.0 |
| Magnesium Stearate | 1.0 |

Tablets at a total weight of 300 mg made from the above formulation exhibited low tablet hardness as measured by a Schleuniger Model 2-E tablet hardness tester, typically 8 kP (kilopon). By contrast, tablets made as in Example 1 at a total weight of 450 mg exhibited a hardness of 11 –15 kP. Hardness is an important physical property of tablets because soft tablests can erode during handling, shipping, and film-coating. Preferred trovafloxacin tablets have a hardness greater than 8 kP.

Tablets made from the above formulation exhibited a suppressed dissolution profile (average of 82% dissolution of Polymorph 1 in 30 minutes) thus failing the USP Stage 1 ($S_1$) criterion described in Example 3.

Tablets made as in Example 1 exhibited faster dissolution (96% dissolution of Polymorph II in 30 minutes).

EXAMPLES 6 to 22

The following examples are formulations made by dry granulation, either by roller compaction or slugging, within the scope of the invention.

| | Formulation Examples for Trovafloxacin Mesylate-containing tablets[1] | | | | | | | | | | | | | | | | | |
|---|---|---|---|---|---|---|---|---|---|---|---|---|---|---|---|---|---|---|
| Examples | 6 | 7 | 8 | 9 | 10 | 11 | 12 | 13 | 14 | 15 | 16 | 17 | 18 | 19 | 20 | 21 | 22 |
| Trovafloxacin Mesylate | 78.3 | 39.5 | 31.6 | 52.7 | 52.7 | 52.7 | 52.7 | 52.7 | 52.7 | 52.7 | 52.7 | 52.7 | 59.3 | 47.0 | 52.7 | 33.9 | 78.3 |
| Microcrystalline Cellulose | 8.9 | 50.0 | 57.9 | 35.6 | 37.8 | 37.7 | 36.8 | 31.6 | 36.8 | 34.7 | 36.8 | 36.8 | 22.9 | 43.3 | 37.8 | 48.4 | 11.5 |
| Sodium Starch Glycolate | — | — | — | — | — | — | 4.8 | 10.0 | — | — | — | — | 10.0 | — | — | 10.0 | — |
| Sodium Croscarmellose | 7.1 | 4.8 | 4.8 | 6.0 | 4.8 | 4.8 | — | — | — | 4.8 | 4.8 | 4.8 | — | — | 4.8 | — | — |
| Polyvinylpyrrolidone-XL | — | — | — | — | — | — | — | 4.8 | — | — | — | — | 6.0 | — | — | 5.5 |

-continued

Formulation Examples for Trovafloxacin Mesylate-containing tablets[1]

| Examples | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|
| Magnesium Stearate | 1.9 | 1.9 | 1.9 | 1.9 | 0.9 | 1.9 | 1.9 | 1.9 | 1.9 | — | — | 1.9 | — | — | 1.9 | 0.9 | — |
| Sodium Stearyl Fumarate | — | — | — | — | — | — | — | — | — | 4.0 | — | — | 4.0 | — | — | 2.0 | — |
| Calcium Stearate | — | — | — | — | — | — | — | — | — | — | 1.9 | — | — | 0.9 | — | — | 1.9 |
| Opadry Blue (Y-5-10670) | 3.8 | 3.8 | 3.8 | 3.8 | 3.8 | 2.9 | 3.8 | 3.8 | 3.8 | 3.8 | 3.8 | — | — | 2.8 | — | — | — |
| Opadry White (Y-5-7068) | — | — | — | — | — | — | — | — | — | — | — | 3.8 | 3.8 | — | 2.8 | 4.8 | 2.8 |

[1]The numbers are expressed as percentage (%, w:w)
* Polymorph I

What is claimed is:

1. A dry granulated composition comprising the polymorph II form of trovafloxacin mesylate, a lubricant, and at least 5% of microcrystalline cellulose (MC).

2. A composition as defined in claim 1, in the form of a tablet.

3. A composition as defined in claim 1 which passes USP, 23rd Edition, Stage 1 ($S_1$) acceptance criteria.

4. A composition as defined in claim 2, further comprising a film coating.

5. A composition as defined in claim 4, wherein said coating comprises hydroxypropyl cellulose.

6. A composition as defined in claim 1, comprising at least 20% by weight of microcrystalline cellulose.

7. A composition as defined in claim 6, comprising at least 30% by weight of microcrystalline cellulose.

8. A composition as defined in claim 2, further comprising a disintegrant.

9. A composition as defined in claim 2, having a hardness of at least 8 kP.

10. A composition of matter comprising trovafloxacin mesylate in the form of a pharmaceutical tablet which, after having been stability tested by being stored for 12 weeks in an open container at constant conditions of 40° C and 75% relative humidity, exhibits the following degradant levels:

A. less than 0.5% by weight of each of N-stearoyltrovafloxacin and N-palimitoyltrovafloxacin;
   B. less than 0.2% by weight of any other degradant; and
   C. the total of (A)+(B) is less than 1.0% by weight.

11. A composition as defined in claim 10, further comprising a film coating.

12. A composition as defined in claim 11, wherein said coating comprises hydroxypropyl cellulose.

13. A composition as defined in claim 10, comprising at least 5% by weight of microcrystalline cellulose.

14. A composition as defined in claim 13, comprising at least 20% by weight of microcrystalline cellulose.

15. A composition as defined in claim 14, comprising at least 30% by weight of microcrystalline cellulose.

16. A composition comprising

| Component | %, w:w |
|---|---|
| Trovafloxacin Mesylate* | 52.7 |
| Microcrystalline Cellulose | 36.8 |
| Sodium Croscarmellose | 4.8 |
| Magnesium Stearate | 1.9 |
| Film Coating | 3.8 |

*polymorph II

* * * * *